United States Patent [19]

Roper

[11] Patent Number: 4,800,230

[45] Date of Patent: Jan. 24, 1989

[54] PREPARATION OF ALPHA-CYANO-PHENOXYBENZYL ESTERS

[75] Inventor: Jerry M. Roper, Baton Rouge, La.

[73] Assignee: Ethyl Corporation, Richmond, Va.

[21] Appl. No.: 880,039

[22] Filed: Jun. 30, 1986

[51] Int. Cl.$^4$ .................... C07C 61/04; C07C 121/52
[52] U.S. Cl. .................................................. 558/388
[58] Field of Search ................ 558/388; 560/217, 234

[56] References Cited

U.S. PATENT DOCUMENTS 2,449,994  9/1948  Gresham et al. ................ 560/234
3,835,176  9/1974  Matsuo et al. .................. 558/388

Primary Examiner—Anton H. Sutto
Attorney, Agent, or Firm—W. G. Montgomery

[57] ABSTRACT

Alpha-cyano-phenoxybenzyl esters are prepared by reacting an acid halide with an ester of an alpha-cyano-phenoxybenzyl alcohol in the presence of an inert polar aprotic solvent and a transition metal alkoxide catalyst.

7 Claims, No Drawings

PREPARATION OF ALPHA-CYANO-PHENOXYBENZYL ESTERS

FIELD OF THE INVENTION

This invention relates to an improved process for preparing alpha-cyano-phenoxybenzyl esters. More particularly, the invention relates to an improved process for preparing alpha-cyano-phenoxybenzyl esters involving an acyl interchange between an acid halide and an ester of an alpha-cyano-phenoxybenzyl alcohol. The compounds produced by the process are known synthetic pyrethroids having pesticidal activity.

BACKGROUND OF THE INVENTION

The cyano-containing phenoxybenzyl esters prepared by the process of the present invention are cyclopropane carboxylic acid esters and phenylacetic acid esters defined by the formula:

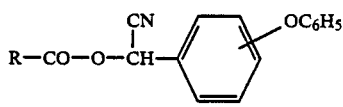

in which R is an optionally substituted cyclopropyl group or an optionally substituted benzyl group. These compounds are significant in that they possess good pesticidal activity yet are low in toxicity with respect to warm blooded mammals. Such compounds are described, for example, in U.S. Pat. No. 4,061,664 incorporated herein by reference. Several methods are known for preparing these compounds including, for example, the method described in aforementioned U.S. Pat. No. 4,061,664 in which an aqueous solution of a carboxylic acid is neutralized and then contacted with a solution of a phenoxybenzyl halide in a water-immiscible base in the presence of a phase transfer catalyst. Other methods of preparation include (i) reacting an acid ester such as ethyl 3-(2,2-dichlorovinyl)-2,2-dimethyl cyclopropane carboxylate, also referred to as "DV-acid ester", with alpha-cyano-phenoxybenzyl alcohol in the presence of a transition metal alkoxide catalyst, (ii) reacting an acid halide such as "DV-acid halide" with m-phenoxybenzaldehyde in the presence of sodium cyanide and a phase-transfer catalyst such as tetrabutylammonium chloride, and (iii) reacting an alpha-cyano-phenoxybenzyl alcohol possessing an alpha-cyano structure with a cyclopropane carboxylic acid halide or a phenylacetyl halide to form the corresponding cyano-containing phenoxybenzyl ester. For example, 3-phenoxy-alpha-cyanobenzyl-3-(2,2-dichlorovinyl)-2,2-dimethylcyclopropane carboxylate, also known as cypermethrin, (trademarked Ripcord ® by Shell and Imperator ® by ICI) can be produced by method (iii) by reacting 3-(2,2-dichlorovinyl)2,2-dimethyl-cyclopropane carboxylic acid chloride with alpha-cyano-phenoxybenzyl alcohol.

It has now been found that the cyano-containing esters of the present invention can be prepared by reacting an acid halide with an ester of an alpha-cyano-phenoxybenzyl alcohol. A particular advantage of the present process resides in the utilization of an ester reactant in lieu of an alpha-cyano-phenoxybenzyl alcohol reactant. In those processes requiring alpha-cyano-phenoxybenzyl alcohol, the alcohol reactant can decompose to the corresponding phenoxybenzaldehyde during storage and, to a lesser extent, during formation of the final pyrethroid product. This is undersirable since toxic hydrogen cyanide is liberated during transformation and product yields are decreased due to the loss of alcohol reactant during transformation. In the past, manufacturers and/or suppliers of the cyanohydrin reactant have sought to remedy this situation by adding acidic agents such as sulfuric acid or p-toluenesulfonic acid to the reagent prior to shipment to maintain the cyanohydrin in a protinated form. While this has proven to be reasonably effective, the addition of an acidic agent to the reagent increases the cost of the reagent to the user and must be removed from the final pyrethroid product prior to its application and use. Thus, a welcome contribution to the art would be the provision of an industrial process for the manufacture of alpha-cyano-phenoxybenzyl esters which does not require the use of an alcohol reactant and thereby avoids the problems of decreased pyrethroid production and hydrogen cyanide liberation.

SUMMARY OF THE INVENTION

In accordance with the present invention, there is provided a process for preparing alpha-cyano-phenoxybenzyl esters of the formula:

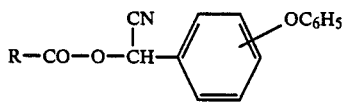

in which an acid halide of the formula:

in which R is an optionally substituted cyclopropyl group or an optionally substituted benzyl group and X is fluorine, chlorine or bromine is reacted with an ester of an alpha-cyano-phenoxybenzyl alcohol of the formula:

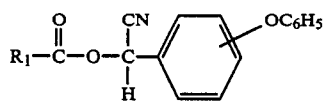

in which $R_1$ is a straight chain or branched chain alkyl group containing from 1 to 6 carbon atoms in the presence of an inert polar aprotic solvent and a transition metal alkoxide catalyst.

The process involves an acyl interchange between the ester reactants and the carboxylic acid derivative reactants used in the process.

In the phenoxybenzyl esters of the present invention, R is either (i) a cyclopropyl group of the formula

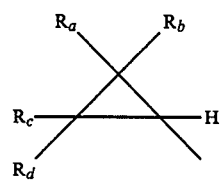

wherein $R_a$ and $R_b$ each represent an alkyl group having from 1 to 6 carbon atoms, preferably methyl, or a halogen atom selected from fluorine, chlorine or bromine; or $R_a$ and $R_b$ together represent an alkylene group having from 2 to 6 carbon atoms; or $R_a$ represents a hydrogen atom and $R_b$ represents an alkenyl group having from 2 to 6 carbon atoms, or a haloalkenyl group having from 2 to 6 carbon atoms and from 1 to 3 chlorine or bromine atoms, especially a mono- or dichlorovinyl group; $R_c$ and $R_d$ each represent an alkyl group having from 1 to 6 carbon atoms, preferably methyl, or $R_c$ is hydrogen and $R_d$ is an alkenyl group having from 2 to 6 carbon atoms, or a haloalkenyl group having from 2 to 6 carbon atoms and from 1 to 3 chlorine or bromine atoms, especially a mono- or dichlorovinyl group; or $R_c$ and $R_d$ together represent an alkylene group having from 2 to 6 carbon atoms; or R can be (ii) a benzyl group of the formula:

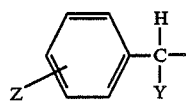

wherein Z represents a halogen atom selected from fluorine, chlorine or bromine or an alkoxy group of 1 to 4 carbon atoms and Y represents a straight chain or branched chain alkyl group of 1 to 6 carbon atoms.

Specific examples of alpha-cyano-phenoxybenzyl esters which can be prepared by the process of the present invention include the alpha-cyano-3-phenoxybenzyl esters of tetramethylcyclopropane carboxylic acid, dimethyl-dichlorovinyl-cyclopropane carboxylic acid, dimethyl-dibromovinyl-cyclopropane carboxylic acid, and the alpha-cyano-3-phenoxybenzyl ester of 2-(4-chlorophenyl)-3-methyl butyric acid. Because of the asymmetric carbon atoms and double bonds which may be present in the structure of the phenoxybenzyl ester compounds produced by the process of the present invention, the compounds can exist in a number of stereoisomeric forms and the present process can be used to produce any one or a mixture of such stereoisomers. The required stereoisomer or mixture of stereoisomers may be obtained by using, as the starting materials, the appropriate isomeric carboxylic acid halide and/or the appropriate stereoisomers of the alpha-cyano-3-phenoxybenzyl ester reactant.

The acid halide reactant of the present process is represented by the formula:

in which R is as defined above and X is fluorine, chlorine or bromine. The acid halide reactants are known compounds and are readily prepared, for example, by reacting the corresponding acid with a halide such as thionyl chloride, phosgene or phosphorus halide.

The ester reactants used in the practice of the process are known compounds as are methods for their preparation. For example, racemic mixtures of (R,S) alpha-cyano-3-phenoxybenzyl esters are obtained by reacting an alkali metal cyanide such as sodium cyanide with 3-phenoxybenzylaldehyde and acetyl chloride in methylene chloride containing tetrabutylammonium bromide as described in Chem. Absts., 96 (25):217504j.

In the practice of the present process, the acid halide and the alpha-cyano-phenoxybenzyl ester components are reacted in substantially equimolar proportions although an excess of acid halide can be used in order to insure complete reaction. The reaction is conveniently carried out in an inert polar aprotic solvent to facilitate a smooth progression of the reaction. Specific examples of solvents which may be used in the process include, but are not limited to, dimethylsulfoxide, acetonitrile, N,N-dimethylformamide, N,N-dimethylacetamide, glyme, diglyme, diethyl ether, diisopropyl ether, acetone, methyl ethyl ketone and chlorinated hydrocarbons such as dichloromethane and chloroform.

Although the reaction will proceed slowly at room temperature, the reaction is more advantageously carried out at an elevated temperature, preferably from about 40° C. to about 100° C. The maximum elevated temperature at which the reaction can be carried out will ultimately be determined by the decomposition temperature of the reaction products and the reactants used in the process.

The use of a transition metal alkoxide catalyst is required in the practice of the process in order to coordinate with the ester reactant to facilitate both the leaving of the acyl moiety of the ester reactant and its subsequent replacement by the functional group of the acid halide reactant. Examples of suitable catalysts which can be employed in the process include titanium tetrabutoxide, titanium tetraisopropoxide, titanium ethoxide and the corresponding transition metal alkoxides of zirconium, manganese, cobalt, nickel and the like. The concentration of catalyst used in the process can vary widely. In general, amounts of from about 10 mole percent up to about 50 mole percent based on the amount of ester reactant used in the process is sufficient to effect complete acyl interchange within an acceptable period of time. If desired, the reaction can be carried out in an inert atmosphere, e.g. under nitrogen.

The invention is further illustrated by the following examples:

EXAMPLE 1

A solution of (S) alpha-cyano-3-phenoxybenzyl acetate (0.27 gram; 1.0 millimole) in diisopropyl ether (10 milliliters) was treated in a 100 milliliter round bottom flask with titanium tetrabutoxide (0.17 gram; 0.5 millimole) to give a red reaction mixture. The mixture was heated to reflux under a nitrogen atmosphere and a solution of chrysanthemoyl chloride (0.37 gram; 2.0 millimole) in isopropyl ether (10 milliliters) was added dropwise over a period of 45 minutes to the flask and the resultant reaction mixture was refluxed for 30 minutes. The mixture was then cooled and quenched with water (10 milliliters). The aqueous phase was separated and the isopropyl ether layer was washed twice with water using 10 milliliter portions of water each time, once with a 10% aqueous solution of sodium bicarbonate (10 milliliters) and again with 10 milliliters of water. The solution was then dried over anhydrous magnesium sulfate and concentrated in vacuo to afford an oil (0.44 gram). The oil was purified by column chromatography on silica gel by eluting with a mixture of heptane:ethyl acetate (85:15) to give (S) alpha-cyano-3-phenoxybenzyl 3-(2,2-dimethylvinyl)-2,2-dimethylcyclopropane carboxylate (0.10 gram; 27% yield). Structure was confirmed by NMR and comparison with known compounds. Optical rotation was observed to be +1.9°

(Perkin-Elmer 241 Polarimeter) indicating chirality was preserved.

EXAMPLE 2

A solution of (R,S) alpha-cyano-3-phenoxybenzyl acetate (0.27 gram; 1.0 millimole) in diisopropyl ether (5.0 milliliters) was treated in a 100 milliliter round bottom flask with titanium tetrabutoxide (0.34 gram; 1.0 millimole) to give a red reaction mixture. The mixture was heated to reflux under a nitrogen atmosphere for about 10 minutes. After cooling to room temperature, a solution of butyryl chloride (0.42 gram; 4.0 millimoles) in isopropyl ether (5.0 milliliters) was added dropwise to the flask and the resultant mixture was stirred for about 1 hour. The mixture was then quenched with water (10 milliliters). The aqueous phase was separated and the isopropyl ether layer was washed 2 times with water (10 milliliter portions each) and once with a 10% aqueous solution of sodium bicarbonate (10 milliliters). The solution was then dried over anhydrous magnesium sulfate and concentrated in vacuo to afford an oil (0.32 gram) which was shown by gas chromatography to contain (R,S) alpha-cyano-3-phenoxybenzyl butyrate (0.27 gram; 90% yield). Structure was confirmed by NMR.

EXAMPLE 3

A solution of (R,S) alpha-cyano-3-phenoxybenzyl acetate (0.27 gram; 1.0 millimole) in diisopropyl ether (10 milliliters) was treated in a 100 milliliter round bottom flask with titanium tetrabutoxide (0.17 gram; 0.5 millimole) to give a red reaction mixture. The mixture was heated to reflux under a nitrogen atmosphere for about 10 minutes. After cooling to room temperature, a solution of butyryl chloride (0.37 gram; 2.0 millimoles) in isopropyl ether (10 milliliters) was added dropwise to the flask and the resultant mixture was stirred for about 1 hour. The mixture was then washed once with a 10% aqueous solution of sodium bicarbonate (10 milliliters) and again with three 10 milliliter portions of water. The solution was dried over anhydrous magnesium sulfate and concentrated in vacuo to afford an oil (0.20 gram) which was shown by gas chromatography to contain (R,S) alpha-cyano-3-phenoxybenzyl butyrate (0.17 gram; 57% yield).

EXAMPLE 4

A solution of (R,S) alpha-cyano-3-phenoxybenzyl acetate (0.27 gram; 1 millimole) in diethyl ether (5.0 milliliters) was treated in a 100 milliliter round bottom flask with titanium tetrabutoxide (0.34 gram; 1.0 millimole) to give a red reaction mixture. The mixture was heated to reflux under a nitrogen atmosphere for 3 hours. After cooling to room temperature, a solution of butyryl chloride (0.42 gram; 4.0 millimoles) in diethyl ether (5.0 milliliters) was added dropwise to the flask and the resultant mixture was stirred for 1 hour. The mixture was then quenched with water (10 milliliters). The aqueous phase was separated and the diethyl ether layer was washed 2 times with water (10 milliliter portions each) and once with a 10% aqueous solution of sodium bicarbonate (10 milliliters). The solution was then dried over anhydrous magnesium sulfate and concentrated in vacuo to afford an oil (0.5 gram) which was shown by gas chromatography to contain (R,S) alpha-cyano-3-phenoxybenzyl butyrate (0.10 gram; 66% yield).

EXAMPLE 5

A solution of (R,S) alpha-cyano-3-phenoxybenzyl acetate (0.27 gram; 1 millimole) in diisopropyl ether (about 10 milliliters) was treated in a 100 milliliter round bottom flask with titanium tetrabutoxide (0.09 gram; 0.25 millimole) to give a red reaction mixture. The mixture was heated to reflux under a nitrogen atmosphere for about 10 minutes and cooled to room temperature. A solution of butyryl chloride (0.13 g; 1.25 millimoles) in isopropyl ether (about 10 milliliters) was added dropwise to the flask at room temperature and the resultant reaction mixture was stirred for about 1 hour. The mixture was then quenched with water (10 milliliters). The aqueous phase was separated and the isopropyl ether layer was washed 2 times with water (10 milliliter portions each) and once with a 10% aqueous solution of sodium bicarbonate (10 milliliters). The solution was then dried over anhydrous magnesium sulfate and concentrated in vacuo to afford an oil (0.27 gram) which was shown by gas chromatography to contain (R,S) alpha-cyano-3-phenoxybenzyl butyrate (0.11 gram; 37% yield).

I claim:

1. A process for the preparation of an alpha-cyanophenoxybenzyl ester of the formula:

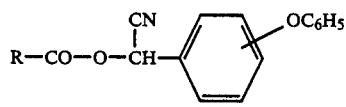

in which an acid halide of the formula:

in which R is an optionally substituted cyclopropyl group or an optionally substituted benzyl group and X is fluorine, chlorine or bromine is reacted with an ester of an alpha-cyano-phenoxybenzyl alcohol of the formula:

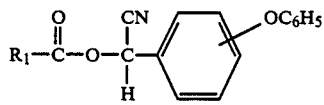

in which $R_1$ is a straight chain or branched chain alkyl group containing from 1 to 6 carbon atoms in the presence of an inert polar aprotic solvent and a transition metal alkoxide catalyst.

2. A process for the preparation of an alpha-cyanophenoxybenzyl ester of the formula:

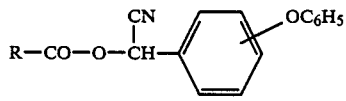

in which an acid halide of the formula:

in which R is
(i) a cyclopropyl group of the formula

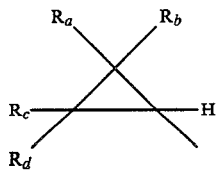

in which $R_a$ and $R_b$ each is an alkyl group containing from 1 to 6 carbon atoms, or a halogen atom selected from flourine, chlorine or bromine, or $R_a$ is a hydrogen atom and $R_b$ is an alkenyl group containing from 2 to 6 carbon atoms optionally substituted with from 1 to 3 chlorine or bromine atoms, $R_c$ and $R_d$ each is an alkyl group containing from 1 to 6 carbon atoms, or $R_c$ is hydrogen and $R_d$ is $R_b$, or $R_a$ and $R_b$ together or $R_c$ and $R_d$ together is an alkylene group containing from 2 to 6 carbon atoms; or R is
(ii) a benzyl group of the formula

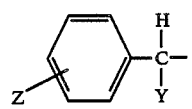

in which Z is a halogen atom selected from flourine, chlorine or bromine or an alkoxy group containing from 1 to 4 carbon atoms and Y is a straight chain or branched chain alkyl group containing from 1 to 6 carbon atoms is reacted with an ester of an alpha-cyano-phenoxybenzyl alcohol of the formula:

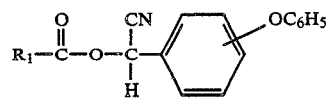

in which $R_1$ is a straight chain or branched chain alkyl group containing from 1 to 6 carbon atoms in the presence of an inert polar aprodic solvent and a transition metal alkoxide catalyst.

3. A process according to claim 2 wherein said solvent is isopropyl ether.

4. A process according to claim 2 wherein said solvent is diethyl ether.

5. A process according to claim 2 wherein said catalyst is titanium tetrabutoxide.

6. A process according to claim 2 wherein said process is carried out from a temperature of about 40° C. to about 100° C.

7. A process according to claim 1 wherein said phenoxybenzyl ester is an alpha-cyano-3-phenoxybenzyl ester of tetramethylcyclopropane carboxylic acid, dimethyl-dichlorylvinyl-cyclopropane carboxylic acid, dimethyl-dibromovinyl-cyclopropane carboxylic acid or 2-(4-chlorophenyl)-3-methylbutyric acid.

* * * * *